United States Patent [19]

Nash

[11] 4,283,175
[45] Aug. 11, 1981

[54] DENTAL SCALER HAVING SCALING TIP WITH ROUNDED EDGE WORK SURFACES PARTICULARLY SUITABLE FOR CIRCULAR OR ELLIPSOIDAL PATTERNS OF VIBRATION

[75] Inventor: John E. Nash, Downingtown, Pa.

[73] Assignee: Syntex (U.S.A.) Inc., Palo Alto, Calif.

[21] Appl. No.: 91,018

[22] Filed: Nov. 5, 1979

[51] Int. Cl.³ ............................................. A61C 1/07
[52] U.S. Cl. .................................... 433/119; 433/165
[58] Field of Search ......................... 433/86, 119, 165; 51/59 SS; 74/1 SS

[56] References Cited

U.S. PATENT DOCUMENTS

| | | | |
|---|---|---|---|
| 3,817,141 | 6/1974 | Simonetti | 74/1 SS |
| 3,930,173 | 12/1975 | Banko | 433/86 |

Primary Examiner—Robert Peshock

Attorney, Agent, or Firm—John A. Dhuey; Joseph I. Hirsch

[57] ABSTRACT

A powered dental scaler is disclosed of a type which drives a vibrating scaling tip in a circular or ellipsoidal pattern of motion. A scaling tip having working surfaces provided by the edges of an elongated, curved element which has a cross-sectional configuration in the shape of a multi-sided figure, e.g., a triangle or a diamond, is particularly useful with a scaler having this type of vibrational pattern. Each of the longitudinal edges has a radius of curvature in the range of about 0.001 inch to about 0.005 inch. The free end of the scaler work tool preferably terminates in rounded or ball-shaped configurations, and the working surfaces can be joined along inactive edges by a convex surface to provide "safe" surfaces. The absence of sharp edges or points on the scaler tool work surfaces substantially reduces the likelihood of damage to tooth dentin, cementum or gums.

61 Claims, 14 Drawing Figures

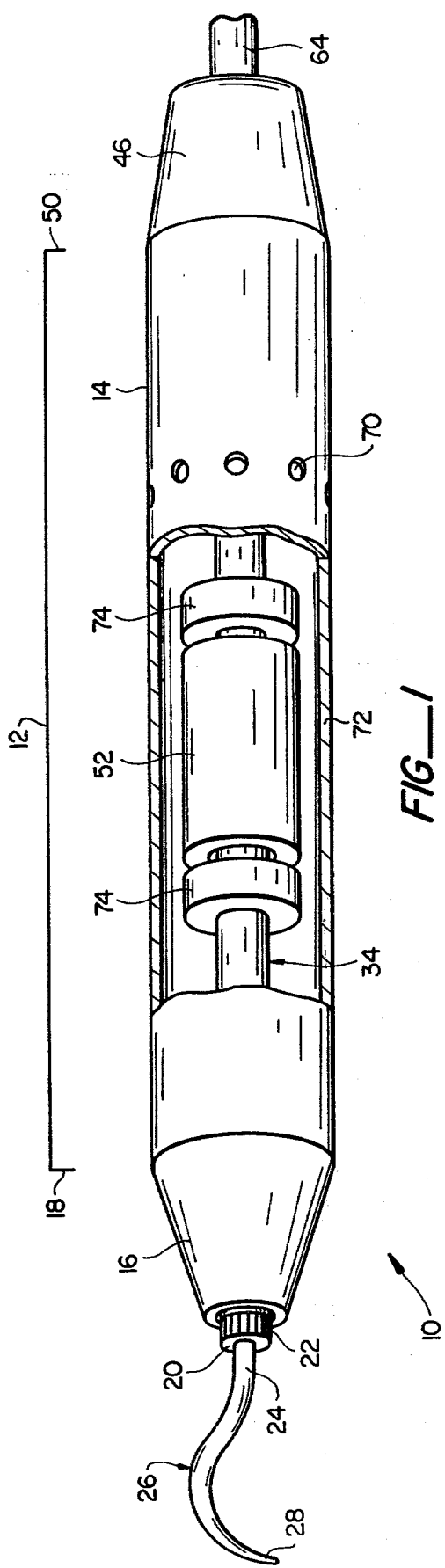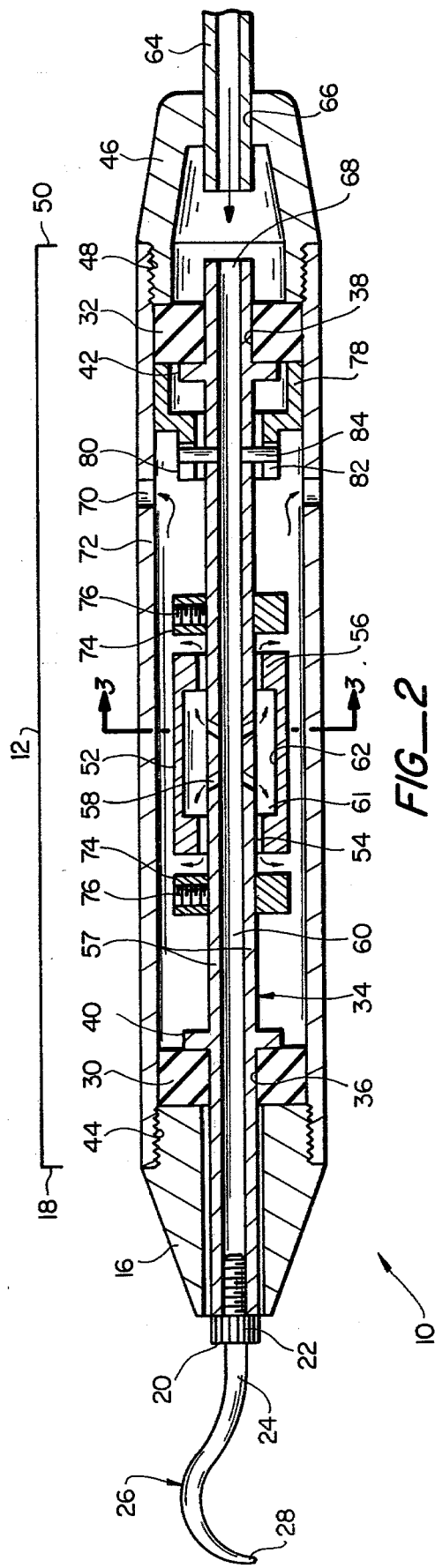

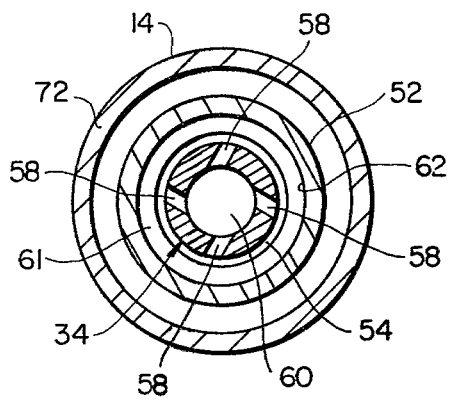
FIG_3
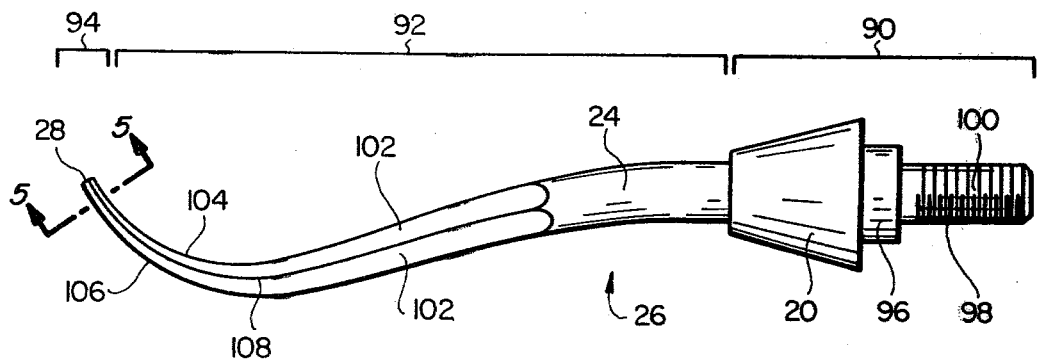
FIG_4
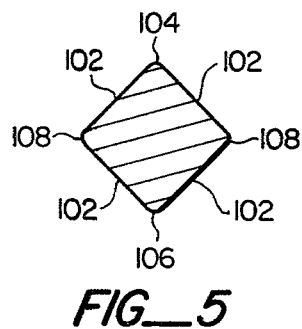
FIG_5
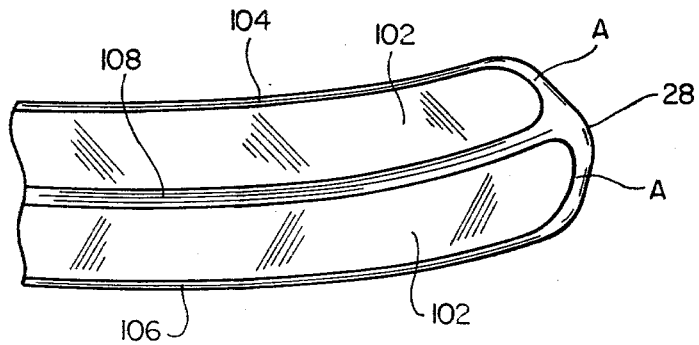
FIG_6

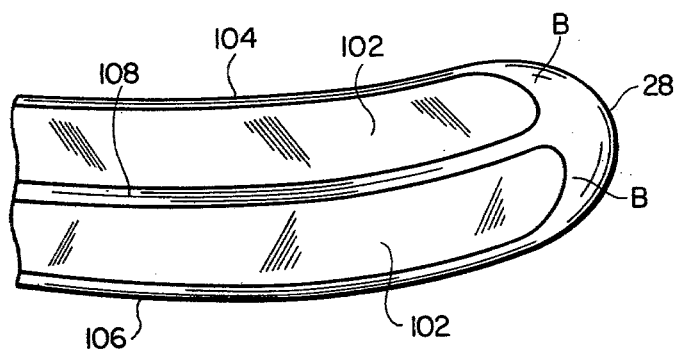
FIG_7
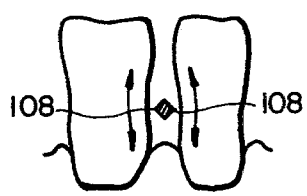 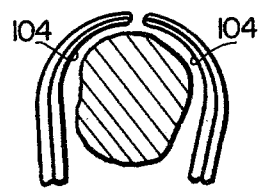 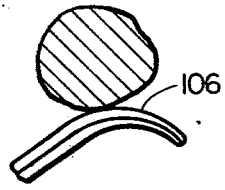
FIG_8  FIG_9A  FIG_9B
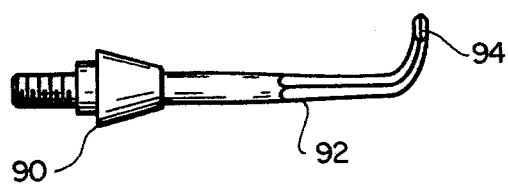 
FIG_10  FIG_11
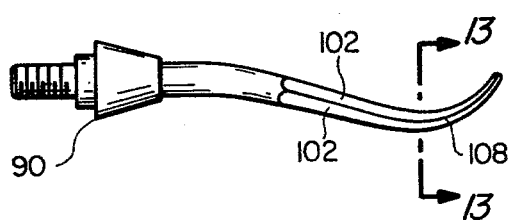 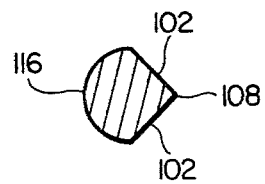
FIG_12  FIG_13

DENTAL SCALER HAVING SCALING TIP WITH ROUNDED EDGE WORK SURFACES PARTICULARLY SUITABLE FOR CIRCULAR OR ELLIPSOIDAL PATTERNS OF VIBRATION

BACKGROUND OF THE INVENTION

1. Field

Power driven dental scalers are well known. Of particular interest herein is a dental scaler having a scaling tip with an improved work surface configuration.

2. State of the Art

Of the power driven dental scalers currently available, most common are scalers utilizing compressed air or an electrical ultrasonic transducer to cause the scraping type work tool to vibrate.

Typical of the earlier air-driven dental scalers are those of U.S. Pat. No. 3,820,529 and U.S. Pat. No. 3,444,622 to Mills et al, which scalers utilize an air-driven ball contained in a chamber. Movement of the ball against the walls of the chamber imparts vibration to the chamber which vibrations are then transmitted to the scraping tool. A more recent type of air-driven scaler, described in U.S. Pat. No. 3,526,962 to Fuerst, utilizes a rotatable mandrel which has an irregularly-shaped tip engaged with a reciprocable block in which the mandrel tip is received.

It is characteristically a problem of these air driven scalers that much of the vibrational energy generated by the vibrator motor is transferred to the handle portion of the dental scaler rather than to the scraper work tool. Moreover, the modes of vibration of these scalers may change as moving parts of the vibration generating mechanism wear with time.

In U.S. Pat. No. 3,703,037 to Robinson, there is described a dental scaler which utilizes an electrical ultrasonic transducer to provide constant modes of vibration for coupling with particular types of work tools. One disadvantage of the ultrasonic scaler, however, is the cost of the transducer and its associated ultrasonic generator.

A recent improvement in air-driven dental scalers is disclosed in U.S. Pat. No. Re. 29,687 to Sertich. This dental scaler has very few moving parts as compared to the aforementioned mechanically complicated air-driven scalers and provides efficient transfer of vibrational energy to a scraping-type work tool with relatively little vibration being transferred to the handle portion of the instrument. Moreover, the Sertich-type scaler provides uniform modes of constant vibration which may be matched with the vibratory modes of various types of work tools without the need for any complicated electronic components.

The Sertich-type dental scaler achieves these advantages in part by including a single, rigid vibratable tube mounted on resilient support washers disposed at or near the theoretical vibratory nodes characteristic of the natural vibrational mode of the tube. A work tool, such as a scraper or a pick, is typically secured to the working end of the vibratable tube by a connection between an externally-threaded work tool shank and an internally threaded portion of the tube.

The mode or pattern of vibration of the vibratable tube of the Sertich-type scaler is characteristically one which during one oscillation or cycle of vibration traces a path that may vary from circular to oval or ellipsoidal in shape. It has been found that this particular vibratory orbit provides maximum efficiency of energy transfer from the tube vibrating mechanism to the working tip.

There has been some attention given to the matching of vibratory mode to a particular scaler tip configuration. For example, in U.S. Pat. No. 2,990,616 to Balamuth et al there is described a preferred mode of vibration which is elliptical in configuration. The described elliptical motions of a tapered vibrating tip provide efficient cutting action for forming a hollowed out portion in a hard, dense material such as tooth dentin. The Balamuth patent discloses one tip configuration for use by a dentist in boxing, that is, in preparing cavities of rectangular cross-section. The tip has an arcuate, somewhat tapered shank and is square in cross-section near the working end of the tip. One problem with the Balamuth tip, however, is that the sharp longitudinal edges of the scaling tip may severely damage teeth by chipping or cutting too far into tooth dentin.

There is, therefore, need for a novel scaler tip for use with a dental scaler having a vibratory mode so as to provide efficient scaling without the hazards of damage to teeth or gums.

SUMMARY OF THE INVENTION

A rigid dental scaler tip is provided having an operative end and an end adapted to be secured to a hand-held dental scaler, the operative end terminating in a curved free end, the operative end having a plurality of sides extending over a portion of the working end, a perpendicular cross-section of the operative end at any point along the working dimension thereof being a multi-sided figure, the curved free end lying in a plane passing through the longitudinal dimension of the scaler tip. For certain applications, the curved free end can have a terminal portion lying outside of the plane in which the major portion of the curved free end lies.

The scaler tip of the invention is particularly suitable for use as a work tool connected to an air driven dental scaler comprising elongated casing means having a proximal end and a distal end, resilient support means within the casing means, a substantially rigid shaft within the elongated casing means, the shaft supported within the casing means by the resilient support means, and means for imparting vibration to the resiliently supported shaft to provide vibratory movement to a work tool connected to the shaft. The described multi-sided figure can be any of a triangle, a square, a diamond-shaped figure, a pentagon, or a hexagon. The operative end of the tip can be symmetrical about a plane passing through the longitudinal dimension of the tip. In such a configuration the defined plane passes through two opposed junctions each formed by the intersection of a different pair of two of four sides of the tip. Two of the four sides intersect with each other to form a first junction extending along the inner radius of the curved operative end. The other two of the four sides then intersect with each other to form a second junction, opposite the first junction, extending along the outer radius of the operative end. The first and second junctions lie along a plane passing through the longitudinal dimension of the scaler tip and on which the curved free end lies.

The means for imparting vibration to the resiliently supported rigid shaft to provide vibratory movement to the work tool connected to the rigid shaft can be of a type disclosed in the aforementioned U.S. Pat. No. Re. 29,687, which is incorporated herein by reference.

In the present invention, each of the longitudinal edges of the scaler has a radius of curvature in the range from about 0.001 inch to about 0.005 inch. A scaler edge having a radius of curvature less than about 0.001 inch may seriously damage tooth dentin and cementum during a scaling treatment, while an edge having radius of curvature greater than about 0.005 inch, although potentially less damaging to teeth, does not provide good scaling efficiency. Within the above range of edge curvature, radii of curvature between about 0.001 inch and 0.002 inch are especially advantageous in that good scaling efficiency is provided with minimal tooth damage, for a scaler tip of a size suitable for use in the oral cavity and for energy input typical of the described vibratory instrument.

The free end of the scaler of the present invention is rounded or spherical in shape. It has been found that scalers with sharp points may in some instances wear grooves or holes in teeth during a cleaning or scaling treatment. Typically, the curved surface at the termination of the free end has a radius of curvature in the range from about 0.005 inch to about 0.02 inch, and preferably ranges from about 0.007 inch to about 0.010 inch. The rounded free end of the scaler tip significantly reduces the likelihood of damage to gums and teeth and enhances patient comfort.

In a further, optional aspect of this invention, two non-opposed edges of the scaler tip can be connected together by a smooth, rounded, convex surface. This aspect of the invention is particularly important when scaler tips are prepared for speciality applications requiring use near sensitive areas of the oral cavity. Typically, such a scaler tip utilizes only one working edge formed by the intersection of two planar surfaces on the operative end of the scaler tip. The non-opposed edges of the surfaces are connected together by a smooth, convex surface to minimize damage to teeth and tissue which might inadvertently be contacted by those portions of the scaler tip which are not being used.

DESCRIPTION OF SPECIFIC EMBODIMENTS

The means providing the features and advantages of the present invention are illustrated in the accompanying drawings wherein:

FIG. 1 is a perspective view, partly in section, of a dental scaling instrument;

FIG. 2 is a longitudinal cross-sectional view of the dental scaler of FIG. 1;

FIG. 3 is a cross-sectional view of the vibratory driving mechanism of the dental scaler of FIG. 2 taken along line 3—3;

FIG. 4 is a side elevational view of a scaler tip of this invention;

FIG. 5 is a cross-sectional view of the scaler tip of FIG. 4 taken along line 5—5;

FIGS. 6 and 7 are enlarged fragmentary views showing, in perspective, two suitable free ends for the scaler tips of this invention;

FIG. 8 is a side elevational view of a pair of human incisor teeth with the scaler tip of FIG. 4, shown in section, positioned therebetween;

FIGS. 9A and B are top sectional views of human teeth showing various uses of a scaler tip of this invention;

FIG. 10 is a side elevational view of another embodiment of this invention illustrating a multi-planar scaler tip;

FIG. 11 is a front elevational view of the scaler tip shown in FIG. 10;

FIG. 12 is a side elevational view of a further scaler tip of the invention wherein the tip has a "safe" side; and FIG. 13 is a cross-sectional view of the scaler tip of FIG. 12 taken along line 13—13.

Illustrated in FIG. 1 is a dental scaling instrument 10 comprising a handle 12 which includes a barrel 14 and a neck 16. Attached to the distal end 18 of handle 12 is a nose piece 20 having an outer knurled wall 22. Secured within nose piece 20 is a shank 24 of a work tool 26 having a configuration of a curved scaler tip having a terminal or free end 28. As shown in detail in the cross-sectional view of FIG. 2, handle 12 provides an elongated housing or casing within which are mounted resilient support means comprising a first or front resilient support bushing 30 and a second or rear resilient support bushing 32. Disposed substantially coaxially with respect to elongated handle 12 is a vibratable shaft in the form of a tube 34 which passes through axially disposed openings 36 and 38, respectively, in bushings 30 and 32. Substantial axial movement of tube 34 is prevented by first and second flanges 40 and 42 which rest against bushings 30 and 32, respectively. First support bushing 30 is retained within the elongated casing by neck 16 which is threadedly engaged with inner wall portion 44 at distal end 18 of handle 12. Similarly, cap 46, which is threadedly engaged with an inner wall portion 48 at proximal end 50, retains second support bushing 32 within the elongated casing provided by handle 12.

Disposed about a mid-portion of tube 34 is a sleeve-like rotor 52. As shown in FIG. 2, rotor 52 is disposed substantially coaxially with respect to tube 34, there being annular gaps 54 established between annular-shaped end portions 56 of rotor 52 and adjacent portions of side wall 57 of tube 34. In an actual assembly with rotor 52 at rest, rotor 52 will be supported upon tube 34 so that a portion of each of the annular ends 56 will rest upon side wall portions of tube 34. Located in side wall portions of tube 34 is a plurality of outlet ports 58 which connect passageway 60 of tube 34 to a chamber 61 defined by inner wall 62 of rotor 52 and an adjacent portion of tube side wall 57.

As indicated by the arrows in FIG. 2, a fluid medium, such as compressed air, is supplied from a source (not shown) through a supply tube 64 which passes through an axially disposed opening 66 in cap 46. The flow of compressed air passes into fluid media inlet port 68 and through passageway 60 to fluid media outlet ports 58. The flow of compressed air which exhausts through outlet ports 58 fills chamber 61. The force of impact of the air flows on inner wall 62 of rotor 52 urges rotor 52 to rotate rapidly about tube 34. As shown in FIG. 3, each of outlet ports 58 has an axis which is offset or spaced at a distance from the longitudinal axis of tube 34, such that each port axis does not intersect the axis of tube 34. Thus each of ports 58 directs a jet of air at a glancing angle with respect to the inner wall 62 of rotor 52 so as to impart rotary movement to rotor 52. Also, as shown in FIG. 2, outlet ports 58 are preferably angled with respect to a plane which is perpendicular to tube 34 and which bisects rotor 52, so that air discharged from half of the plurality of ports 58 imparts a component of force tending to move rotor 52 in the distal direction, while flows of air discharged from the other half of the plurality of ports 58 impart a component of force tending to move rotor 52 in the proximal direction.

After imparting rotary movement to rotor 52, the air exhausts from chamber 61 through fluid media outlet ports as provided by annular gaps 54 defined by annular end portions 56 and tube side wall 57. The air is further exhausted from the interior of barrel 14 through exhaust ports 70 disposed circumferentially about a rearward portion 72 of barrel 14. Stop means comprising annular-shaped guides 74 are affixed to tube 34 by set screws 76. Guides 74 are positioned adjacent either end of rotor 52 so as to limit movement of rotor 52 in the axial direction along tube 34.

The speed of revolution of rotor 52 about tube 34 is generally dependent upon the size, number and angles of incidence of the air streams discharged from outlet ports 58, and the velocity thereof. A description of the manner in which the spinning rotor 52 imparts vibration to tube 34 may be found in the aforementioned U.S. Pat. No. Re. 29,687, the disclosure of which is incorporated herein by reference.

It is generally characteristic of the various Sertich-type dental scalers that the mode of vibration as evidenced by a trace of movement of a cross-section of tip 26, taken as shown in FIG. 5, may vary from a circular to an ellipsoidal pattern. The particular pattern traced and the amplitude of vibration is believed to be dependent upon the mass of tip 26, its configuration in cross-section, the vibratory mode of tube 34 and the amount of energy transferred to tip 26 from tube 34.

As shown in FIG. 4, scaler tip 26 has a connectable end portion 90 adapted to be secured to a dental instrument, a working free end portion 94 and a working mid-portion 92. End portion 90 comprises a nose piece or fingergrip 20 having a boss portion 96 to which is affixed a stud 98 having a threaded portion 100. Threaded portion 100 operatively secures scaler tip 26 to tube 34. Scaler mid-portion 92 includes a shank 24 having a generally circular cross-section and which extends into and is frictionally engaged with nose piece 20. Shank 24 comprises about one-quarter the length of mid portion 92, the balance of mid portion 92 having a curved, elongated configuration with four sides 102. A cross-section taken at any point along and substantially perpendicular to the longitudinal axis of scaler mid portion 92 has a configuration of an equilateral, four sided figure. As shown in FIG. 5, the cross-section preferably has the shape of a diamond, i.e., a square tilted on one of its edges.

Scaler tip 26 also includes a working free end portion 94 having a terminal end 28, as shown in FIG. 4. The curved free end portion 94 generally lies in a plane passing through the longitudinal dimension of scaler tip 26 and can be symmetrical about that plane.

Free end 94 and a part of mid-portion 92 are curved so as to form a concave working edge 104 as provided by a first junction or intersection of two adjacent sides 102 and a convex working edge 106 as provided by a second junction or intersection of two other adjacent sides 102, the first and second junctions being in opposed relationship. The described plane of symmetry will thus preferably pass through the two opposed junctions formed by the intersection of different pairs of two of four sides 102. A pair of lateral working edges 108 is provided by opposed third and fourth junctions or intersections as established by the junctions of pairs of opposed sides 102, portions of which third and fourth junctions lie in a plane substantially perpendicular to the first defined plane containing the free end.

Each scaler edge 104, 106 and 108 is curved as shown in in FIGS. 6 and 7, each curve having a radius of curvature in the range of about 0.001 inch to about 0.005 inch. Preferably, each curve has a radius of curvature in the range of about 0.001 inch to about 0.002 inch. It has been found that a scaler having curved edges as specified provides efficient scaling of teeth with minimal damage to teeth and adjacent tissue.

As shown in FIGS. 10 and 11, free end 94 may also be curved away from the longitudinal plane containing curved intermediate portion 92 so that access may be gained to specific regions of the oral cavity. The particular curvature of free end 94 will vary with the nature of the region in which the work is to be performed. A very useful configuration is to have free end 94 lie in a plane perpendicular (or substantially perpendicular) to the plane containing shank 24 and the part of curved portion 92 adjacent thereto.

As another aspect of the scaler tip of the present invention, free end portion 94 of scaler tip 26 has a rounded terminal end 28, as indicated at surface "A" of FIG. 6 and at surface "B" of FIG. 7. Typically, the radius of curvature of rounded terminal end 28, may range from about 0.005 inch to about 0.02 inch, and preferably, about 0.007 inch to about 0.010 inch. Terminal end 28 may be quite "flat" as shown in FIG. 6 or more highly curved as shown in FIG. 7, or may be in the form of a portion of a perfect spherical shape, or could, as well, have a hyperbolic shape, or a parabolic shape, or other smooth curve. One advantage provided by rounded terminal end 28 is that the likelihood of damage to tooth dentin, cementum or gums is materially reduced as compared with use of a sharp pointed terminal end.

To further reduce the likelihood of damage to tooth dentin, cementum or gums, the inactive edges of the scaler tip of the invention can be connected by smooth, convex surfaces. Such convex surfaces present "safe" surfaces away from working edges and permit the use of tips as described in regions of the oral cavity which contain sensitive tissues or in which the potential for damage is high.

Because of the vibrational characteristics of Sertich-type dental scalers, it has been found advantageous to place a working edge along one of the lateral sides of scaler tip 26. The edges on either side of the surfaces forming the working edge can be joined by a smooth, convex surface, thereby resulting in a configuration having a favorable mass distribution for optimal scaling as well as a "safe" side which will not damage teeth or tissue inadvertently contacted during use. Such a configuration is illustrated in FIGS. 12 and 13 wherein lateral working edge 108 is formed by the intersection of surfaces 102. A substantial portion of working edge 108 lies in a first plane substantially perpendicular to a second plane passing through the longitudinal dimension of scaler tip 26 and in which curved free end 94 lies. The remaining portion of edge 108 extends laterally along the side of curved free end 94. The non-intersecting edges of surfaces 102 are joined by convex surface 116, which presents a smooth surface away from working edge 108.

Working edge 108 can be displaced ±15 degrees from the perpendicular plane without substantially affecting the scaling effectiveness of the tip. It is preferred, however, to keep working edge 108 within ±10 degrees of the perpendicular plane. Such variation also has been found acceptable when the working edge lies substantially in the plane passing through the longitudinal dimension of tip 26 and in which curved free end 94 lies. Typically, the plane passing through the longitudinal dimension and in which free end 94 lies bisects the angle formed by the sides intersecting at the working edge, when the working edge is on the inner or outer radii of the curved free end. Such symmetry presents favorable mass distribution for vibratory modes manifested by the Sertich-type scalers which results in rapid cleaning and scaling while maintaining good tactile control and sensitivity for the operator.

The described scaler tip of the invention provides in one work tool several advantageous features. For example, as shown in FIG. 8, lateral edges 108 provide symmetrical scaling on all sides of a tooth and especially provide very good interproximal scaling. It is especially an advantage of the present invention that the circular or ellipsoidal motion of the scaler tip, in combination with the diamond-shaped cross-sectional configuration, provides very efficient and uniform scaling action of deposits from teeth. A second feature of the scaler tip is provided by the curved work surfaces. For example, concave working edge 104 allows cleaning of the sharp curves of teeth as depicted in FIG. 9. Concave edge 104 is suited for cleaning the contours of molars, as shown in FIG. 9A. Convex edge 106 is useful for cleaning and for removing stain from anterior buccal surfaces as shown in FIG. 9B.

The tips of this invention can be utilized with a dental scaler or vibratory device of the type described in Sertich U.S. Pat. No. Re. 29,687 or copending application Ser. No. 91,016, entitled "Rotor Driven Vibratory Device Having Rotor Centralization Means and Vibrational Mode Selection Means Associated Therewith," filed concurrently herewith. If desired, such a dental scaler or vibratory device can be modified in accordance with the teachings of any or all of copending applications Ser. No. 12,631, filed Feb. 16, 1979; Ser. No. 26,378, filed Apr. 2, 1979; and application Ser. No. 91,012, entitled "Vibratory Device Having Tool Assembly With Fluid Transport Means," filed concurrently herewith. The above applications are incorporated herein by reference to the extent necessary to supplement or complete the disclosure hereof.

Although it is presently preferred that the scaler tip of this invention include both the curved edges and the rounded tip, either can be used independently if desired.

While this invention has been described with reference to specific embodiments thereof, it should be understood by those skilled in this art that various changes may be made and equivalents may be substituted without departing from the true spirit and scope of the invention. All such modifications are intended to be within the scope of the claims appended hereto.

What is claimed is:

1. A dental scaler comprising:
   elongated casing means having a proximal end and a distal end;
   resilient support means within said casing means;
   a rigid shaft supported within said elongated casing means by said resilient support means;
   means for imparting vibration to said resiliently supported rigid shaft when said scaler is energized to provide vibratory movement to a work tool connected to said rigid shaft;
   a work tool connected to the distal end of said rigid shaft, said work tool comprising a rigid shank having an operative end and an end adpated to be connected to said rigid shaft, said operative end terminating in a curved free end, said operative end having a plurality of sides extending over a portion of the length thereof, a perpendicular cross-section of said operative and at any point substantially along the entire longitudinal dimension thereof being a multisided figure;
   said multi-sided figure having a plurality of edges, each of said edges provided by an intersection of a pair of adjacent sides of said plurality of sides, said edges extending over a portion of the length of said free end, each of said edges having a radius of curvature in the range from about 0.001 inch to about 0.005 inch.

2. The dental scaler of claim 1 wherein each of said edges has a radius of curvature in the range from about 0.001 inch to about 0.002 inch.

3. The dental scaler of claim 1 wherein said free end is rounded.

4. The dental scaler of claim 3 wherein said rounded free end has a radius of curvature in the range from about 0.005 inch to about 0.02 inch.

5. The dental scaler of claim 1 wherein said figure is diamond-shaped.

6. The dental scaler of claim 1 wherein said operative end is symmetrical about a plane passing through the longitudinal dimension of said work tool.

7. The dental scaler of claim 5 wherein said operative end is symmetrical about a plane passing through the longitudinal dimension of said work tool, the plane also passing through two opposed junctions each formed by the intersection of a different pair of two of the four sides of said diamond-shaped figure.

8. The dental scaler of claim 7 wherein two of said four sides intersect with each other to form a first junction extending along the inner radius of said curved free end; the other two of said four sides intersect with each other to form a second junction, extending along the outer radius of the curved free end; and said first and second junctions lie along the plane passing through the longitudinal dimension of said work tool and on which said curved free end lies.

9. The dental scaler of claim 8 wherein two of said four sides intersect with each other to form a third junction extending generally parallel to said first and second junctions; the other two of said four sides intersect with each other to form a fourth junction extending parallel to said first and second junctions and opposite said third junction; and portions of said third and fourth junctions lie along a plane substantially perpendicular to the plane passing through the longitudinal dimension of said work tool on which said curved free end lies.

10. The dental scaler of claim 1 wherein said means for imparting vibration to said resiliently supported rigid shaft comprises means for imparting vibratory movement to said shaft so that said work tool vibrates in a mode substantially tracing an ellipsoidal-shaped path.

11. The dental scaler of claim 1 wherein said rigid shaft comprises a tube supported along spaced apart portions thereof by said resilient support means, said tube including fluid media inlet means and outlet means, respectively for receiving and discharging fluid media; said means for imparting vibration comprises rotor means operatively associated with said tube and disposed axially parallel with respect to the axis of said tube, said rotor means drivable about said tube by the fluid media;

said tube and said rotor means each having a configuration and disposed with respect to each other so as to define a space therebetween for receiving the fluid media during movement of said rotor means with respect to said tube;

whereby fluid media flowing through said inlet means into the space drives said rotor means rotatably with respect to said tube so that said rotor means imparts vibratory movement to said tube.

12. The dental scaler of claim 11 wherein said fluid media inlet means comprises an opening in one end of said tube adjacent the proximal end of said casing;

said fluid media outlet means comprises one or more ports in the sidewall of said tube, each of said ports having an axis spaced from the longitudinal axis of said tube;

said rotor means is a sleeve having an inner diameter slightly greater than the outer diameter of said tube, and said sleeve is disposed with respect to said tube so that one or more of said tube outlet ports may discharge fluid media into the space between said sleeve and said tube.

13. The dental scaler of claim 1, claim 2, claim 3, claim 4 or claim 5 wherein said curved free end has a portion thereof lying in a first plane passing through the longitudinal dimension of said operative end and a terminal portion lying outside of said first plane.

14. The dental scaler of claim 13 wherein said terminal portion lies in a second plane substantially perpendicular to said first plane.

15. The dental scaler of claim 1 wherein said curved free end has a first portion thereof lying in a first plane passing through the longitudinal dimension of said operative end and a second, terminal portion lying outside of said first plane, said portion lying in said first plane being symmetrical about said first plane.

16. The dental scaler of claim 15 wherein said first plane also passes through two opposed junctions each formed by the intersection of a different pair of two of the sides of said multi-sided figure.

17. The dental scaler of claim 16 wherein said multi-sided figure is diamond-shaped.

18. The dental scaler of claim 17 wherein two of the four sides of said diamond-shaped figure intersect with each other to form a first junction extending along the inner radius of said first portion of said curved free end; the other two of said four sides intersect with each other to form a second junction, extending along the outer radius of said first portion of said curved free end; and said first and second junctions lying in said first plane.

19. The dental scaler of claim 18 wherein two of said four sides intersect with each other to form a third junction extending generally parallel to said first and second junctions; the other two of said four sides intersect with each other to form a fourth junction extending parallel to said first and second junctions and opposite said third junction; and portions of said third and fourth junctions lying along a plane substantially perpendicular to said first plane and passing through the longitudinal dimension of said work tool.

20. A dental scaler comprising:

elongated casing means having a proximal end and a distal end;

resilient support means within said casing means;

a rigid shaft supported within said elongated casing means by said resilient support means;

means for imparting vibration to said resiliently supported rigid shaft when said scaler is energized to provide vibratory movement to a work tool connected to said rigid shaft;

a work tool connected to the distal end of said rigid shaft, said work tool comprising a rigid shank having an operative end and an end adapted to be connected to said rigid shaft, said operative end terminating in a curved free end, said operative end having at least two generally planar sides extending along a portion of the length thereof and intersecting at a junction to define a longitudinal working edge, said operative end further having at least one pair of longitudinally extending non-intersecting edges and a convex surface joining said longitudinally extending non-intersecting edges, said working edge having a radius of curvature in the range from about 0.001 inch to about 0.005 inch.

21. The dental scaler of claim 20 wherein said working edge has a radius of curvature in the range from about 0.001 inch to about 0.002 inch.

22. The dental scaler of claim 20 wherein said free end is rounded.

23. The dental scaler of claim 22 wherein said rounded free end has a radius of curvature in the range from about 0.005 inch to about 0.02 inch.

24. The dental scaler of claim 20, claim 21, claim 22, or claim 23 wherein said curved free end lies in a plane passing through the longitudinal dimension of said tip and substantially bisecting the angle formed by the intersection of said planar sides.

25. The dental scaler of claim 20, claim 21, claim 22 or claim 23 wherein said curved free end lies in a first plane passing through the longitudinal dimension of said tip and within ±15 degrees of perpendicular to a second plane passing through the longitudinal dimension of said tip and a portion of said working edge.

26. The dental scaler of claim 25 wherein said first plane is within ±10 degrees of perpendicular to said second plane.

27. The dental scaler of claim 20, claim 21, claim 22 or claim 23 wherein said curved free end has a first portion thereof lying in a first plane passing through the longitudinal dimension of said operative end and a terminal portion lying outside of said first plane.

28. The dental scaler of claim 27 wherein said terminal portion lies in a second plane substantially perpendicular to said first plane.

29. A dental scaler tip having an operative end and an end adapted to be secured to a hand-held dental scaler, said operative end terminating in a curved free end, said operative end having a plurality of sides extending substantially the entire length thereof, a perpendicular cross-section of said operative end at any point substantially along the entire longitudinal dimension thereof being a multi-sided figure, said multi-sided figure having a plurality of edges, each of said edges provided by an intersection of a pair of adjacent sides of said plurality of sides, said edges extending substantially the entire length of said free end, each of said edges having a radius of curvature in the range from about 0.001 inch to about 0.005 inch.

30. The scaler tip of claim 29 wherein each of said edges has a radius of curvature in the range from about 0.001 inch to about 0.002 inch.

31. The scaler tip of claim 29 wherein said free end is a rounded.

32. The scaler tip of claim 31 wherein said rounded free end has a radius of curvature in the range from about 0.005 inch to about 0.02 inch.

33. The scaler tip of claim 29 wherein said operative end is symmetrical about a plane passing through the longitudinal dimension of said tip.

34. The scaler tip of claim 29 wherein said figure is diamond-shaped.

35. The scaler tip of claim 34 wherein said operative end is symmetrical about a plane passing through the longitudinal dimension of said tip, the plane also passing through two opposed junctions each formed by the intersection of a different pair of two of the four sides of said diamond-shaped figure.

36. The scaler tip of claim 34 wherein two of said four sides intersect with each other to form a first junction extending along the inner radius of said curved free end; the other two of said four sides intersect with each other to form a second junction, opposite said first junction, extending along the outer radius of said curved free end; and said first and second junctions lie along the plane passing through the longitudinal dimension of said scaler tip and on which said curved free end lies.

37. The dental scaler of claim 36 wherein two of said four sides intersect with each other to form a third junction extending generally parallel to said first and second junctions; the other two of said four sides intersect with each other to form a fourth junction extending generally parallel to said first and second junctions and opposite said third junction; and said third and fourth junctions lie along a plane substantially perpendicular to the plane passing through the longitudinal dimension of said work tool on which said curved free end lies.

38. The scaler tip of claim 29, claim 30, claim 31 or claim 32 wherein said curved free end has a first portion thereof lying in a first plane passing through the longitudinal dimension of said operative end and a terminal portion lying outside of said first plane.

39. The scaler tip of claim 38 wherein said terminal portion lies in a second plane substantially perpendicular to said first plane.

40. The scaler tip of claim 38 wherein said first portion of said curved free end is symmetrical about said first plane passing through the longitudinal dimension of said tip.

41. The scaler tip of claim 40 wherein said first plane also passes through two opposed junctions each formed by the intersection of a different pair of two of the sides of said multi-sided figure.

42. The scaler tip of claim 41 wherein said multi-sided figure is diamond-shaped.

43. The scaler tip of claim 42 wherein two of the four sides of said diamond-shaped figure intersect with each other to form a first junction extending along the inner radius of said first portion of said curved free end; the other two of said four sides intersect with each other to form a second junction, opposite said first junction, extending along the outer radius of said first portion of said curved free end; and said first and second junctions lying in said first plane.

44. The dental scaler of claim 43 wherein two of said four sides intersect with each other to form a third junction extending generally parallel to said first and second junctions; the other two of said four sides intersect with each other to form a fourth junction extending generally parallel to said first and second junctions and opposite said third junction; and said third and fourth junctions lying along a plane substantially perpendicular to said first plane and passing through the longitudinal dimension of said work tool.

45. A dental scaler tip having an operative end and an end adapted to be secured to a hand-held dental instrument, said operative end terminating in a curved free end, said operative end having at least two generally planar sides extending along a portion of the length thereof and intersecting at a junction to define a longitudinal working edge, said operative end further having at least one pair of longitudinally extending non-intersecting edges and a convex surface joining said longitudinally extending non-intersecting edges.

46. The scaler tip of claim 45 wherein said curved free end lies in a plane passing through the longitudinal dimension of said tip and substantially bisecting the angle formed by the intersection of said planar sides.

47. The scaler tip of claim 45 wherein said curved free end lies in a first plane passing through the longitudinal dimension of said tip and within ±15 degrees of perpendicular to a second plane passing through the longitudinal dimension of said tip and a portion of said working edge.

48. The scaler tip of claim 47 wherein said first plane is within ±10 degrees of perpendicular to said second plane.

49. The scaler tip of claim 45, claim 46, claim 47 or claim 48 wherein said working edge has a radius of curvature in the range from about 0.001 inch to about 0.005 inch.

50. The scaler tip of claim 49 wherein said working edge has a radius of curvature in the range from about 0.001 inch to about 0.002 inch.

51. The scaler tip of claim 49 wherein said free end is rounded.

52. The scaler tip of claim 51 wherein said rounded free end has a radius of curvature in the range from about 0.005 inch to about 0.02 inch.

53. The scaler tip of claim 45 wherein said curved free end has a first portion thereof lying in a first plane passing through the longitudinal dimension of said operative end and a terminal portion lying outside of said first plane.

54. The scaler tip as in claim 53 wherein said terminal portion lies in a second plane substantially perpendicular to said first plane.

55. The scaler tip of claim 53 wherein said first plane substantially bisects the angle formed by the intersection of said planar sides.

56. The scaler tip of claim 53 wherein said first plane is within ±15 degrees of perpendicular to a third plane passing through the longitudinal dimension of said tip and a portion of said working edge.

57. The scaler tip of claim 56 wherein said first plane is within ±10 degrees of perpendicular to said third plane.

58. The scaler tip of claim 53, claim 54, claim 55, claim 56 or claim 57 wherein said working edge has a radius of curvature in the range from about 0.001 inch to about 0.005 inch.

59. The scaler tip of claim 58 wherein said working edge has a radius of curvature in the range from about 0.001 inch to about 0.002 inch.

60. The scaler tip of claim 58 wherein said free end is rounded.

61. The scaler tip of claim 60 wherein said rounded free end has a radius of curvature in the range from about 0.005 inch to about 0.02 inch.

* * * * *